(12) United States Patent
Logan et al.

(10) Patent No.: US 6,241,219 B1
(45) Date of Patent: Jun. 5, 2001

(54) AIR CIRCULATOR ROOM DEODORIZER

(76) Inventors: Michael A. Logan, P.O. Box 621058, Oviedo, FL (US) 32762; Emae A. Villalobos, 1870 Rex Ct., Longwood, FL (US) 32750

( * ) Notice: Subject to any disclaimer, the term of this patent is extended or adjusted under 35 U.S.C. 154(b) by 0 days.

(21) Appl. No.: 09/409,322

(22) Filed: Sep. 30, 1999

(51) Int. Cl.$^7$ ....................................................... B01F 3/04
(52) U.S. Cl. .................. 261/30; 261/104; 261/DIG. 88; 422/124; 239/56; 239/57; 239/59
(58) Field of Search .................... 261/30, 104, DIG. 88; 422/124; 239/56, 57, 59

(56) References Cited

U.S. PATENT DOCUMENTS

| | | | |
|---|---|---|---|
| D. 308,721 | 6/1990 | Ahl | D23/366 |
| D. 329,282 | 9/1992 | Petersimes, Sr. et al. | D23/366 |
| D. 334,800 | 4/1993 | Portis | D23/366 |
| 1,246,529 | * 11/1917 | Bieder | 261/30 |
| 1,528,640 | * 3/1925 | Tvrzicky et al. | 261/30 |
| 1,687,830 | 10/1928 | Clevenger . | |
| 2,500,896 | * 3/1950 | Drake | 239/57 |
| 2,734,769 | 2/1956 | Holz | 299/24 |
| 3,129,888 | * 4/1964 | O'Hagan | 239/57 |
| 3,754,707 | * 8/1973 | Morane | 239/59 |
| 3,945,568 | 3/1976 | Bychowski | 239/57 |
| 4,523,870 | * 6/1985 | Spector | 239/57 |
| 5,383,598 | * 1/1995 | Styles | 239/57 |
| 5,732,882 | 3/1998 | Gibbs | 239/56 |
| 5,752,658 | 5/1998 | Gibbs et al. | 239/56 |
| 5,935,526 | * 8/1999 | Moore | 422/124 |

* cited by examiner

Primary Examiner—David A. Simmons
Assistant Examiner—Robert A. Hopkins
(74) Attorney, Agent, or Firm—Edward M. Livingston, Esq.

(57) ABSTRACT

An air-circulator room deodorizer has a permeable container (1) that is positioned with an air-circulator attachment (8, 10, 12, 14) in airflow from a room air circulator such as a room fan (3, 5) or vent (4, 6) and has a deodorant pack (18) that releases fragrance selectively into the airflow.

36 Claims, 4 Drawing Sheets

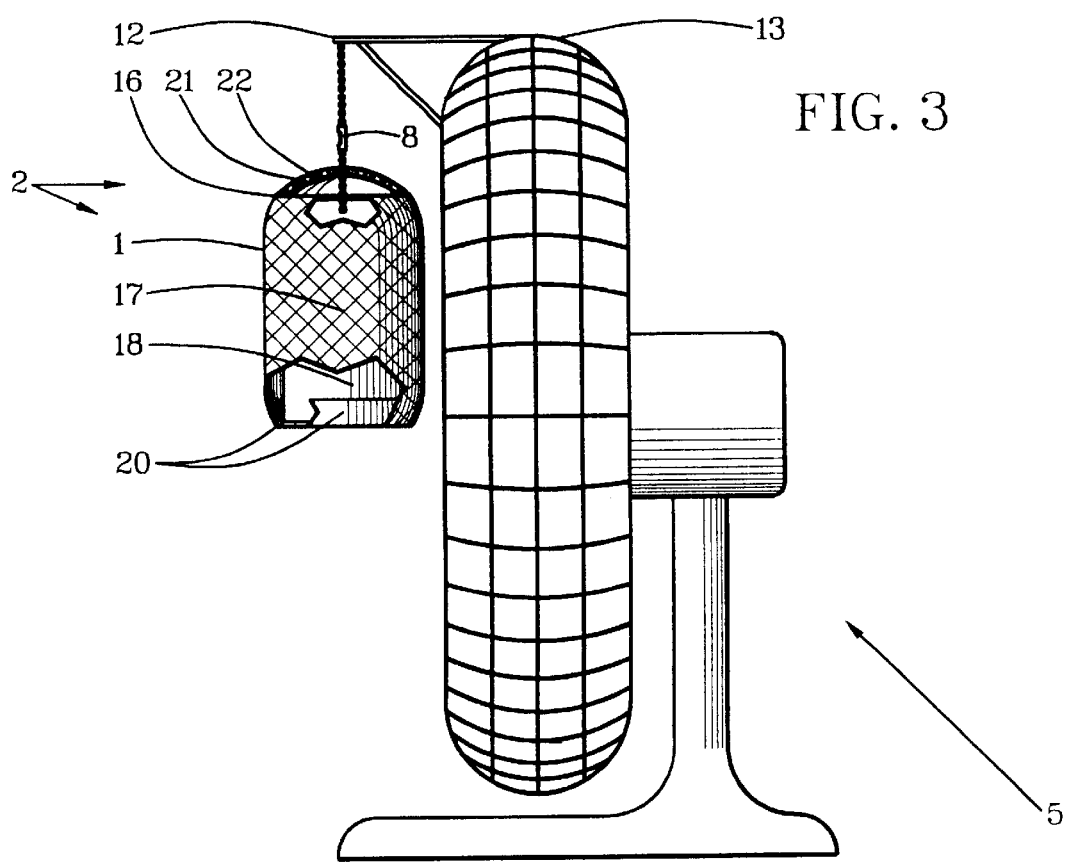
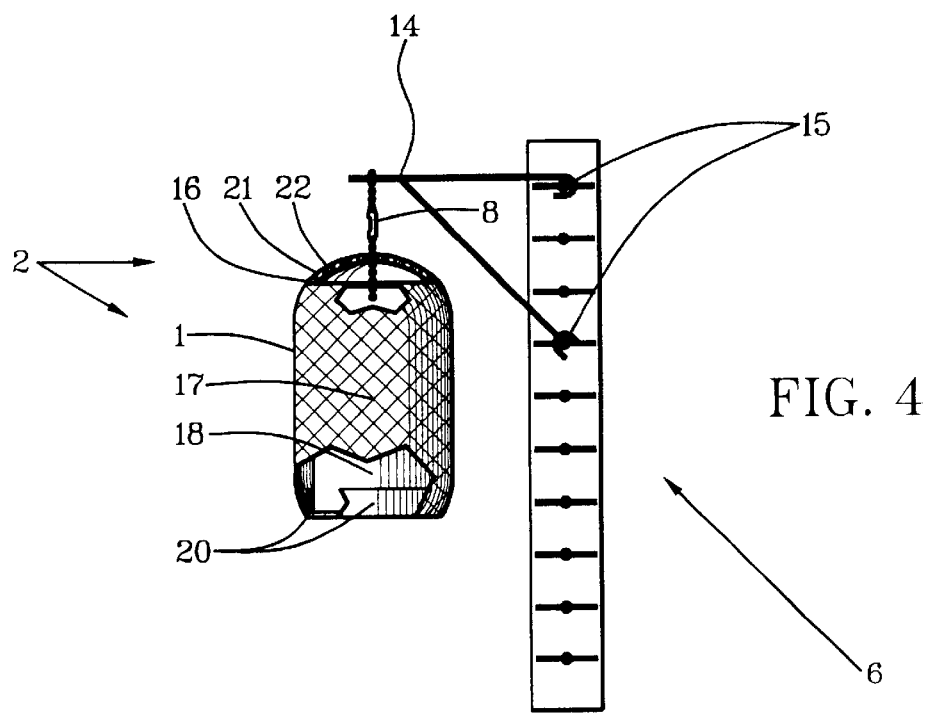

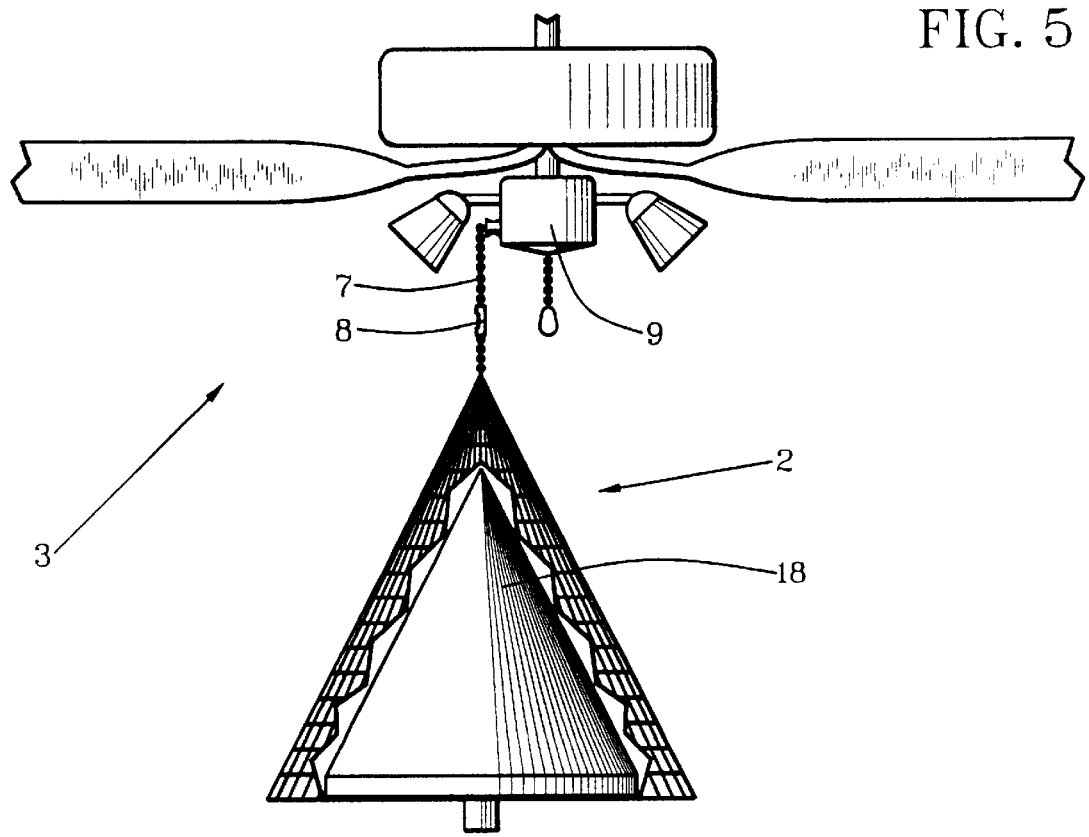
FIG. 5
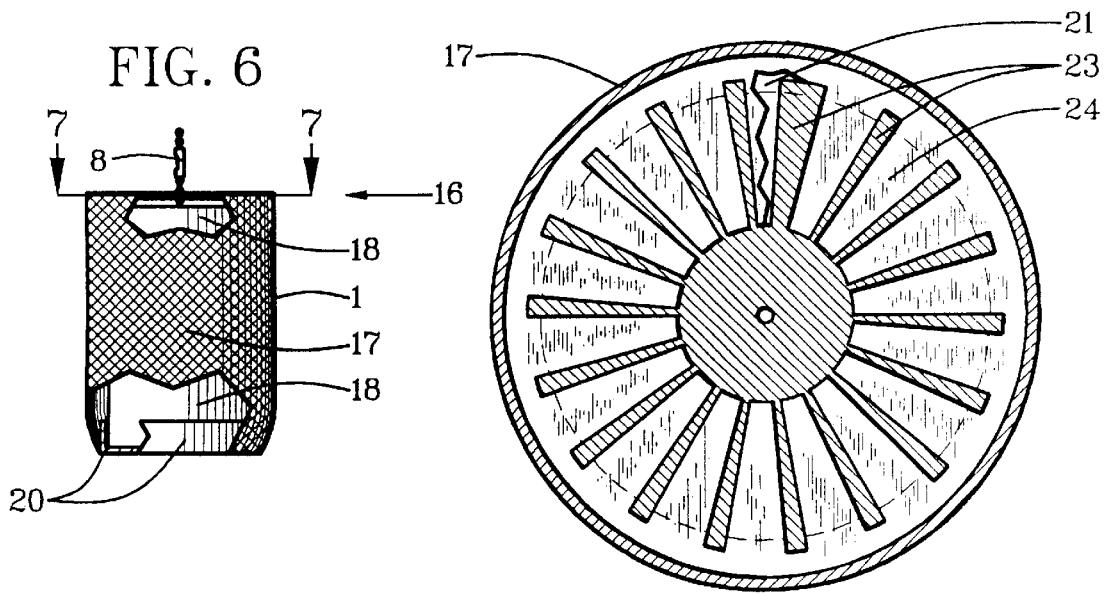
FIG. 6
FIG. 7

AIR CIRCULATOR ROOM DEODORIZER

BACKGROUND OF THE INVENTION

This invention relates to room deodorizers and more particularly to a room deodorizer that is positional in airflow from a room air circulator such as a fan or a vent.

There are known room deodorizers but none with the convenience and effectiveness made possible by this invention.

Examples of different but related room deodorizers are described in the following patent documents. U.S. Pat. Nos. 5,752,658 and 5,732,882, both by the same principle inventor, Gibbs, issued on May 19, 1998 and Mar. 31, 1998, respectively, described vented circular half shells that contained deodorizer for being hung on a chain of a ceiling fan. Design Pat. No. 334,800, issued to Portis on Apr. 13, 1993, showed a hemispherical container of deodorizer that was strapped to a top of a blade of a ceiling fan. Other fan-blade deodorizers also are known. U.S. Pat. No. 1,687,830, issued to Clevenger on Oct. 16, 1928, described a cylindrical container having holes in a top portion and having a bottom portion which contained liquid deodorizer into which a wick was suspended from a cover on the container for drawing the deodorizer up to be encountered by fan-circulated air passing horizontally through the permeability.

SUMMARY OF THE INVENTION

Objects of patentable novelty and utility taught by this invention are to provide an air-circulator room deodorizer which:

positions an effective deodorizer in airflow from a room air circulator such as a fan or an air-conditioner vent;

is easily replenishable with deodorizer; and is adaptable to a wide variety of vertical and horizontal room air circulators.

This invention accomplishes these and other objectives with an air-circulator room deodorizer having a permeable container that is sized and shaped to be positioned in airflow from a room air circulator such as a fan or vent and has a deodorant pack that releases deodorant selectively into the airflow.

The above and other objects, features and advantages of the present invention should become even more readily apparent to those skilled in the art upon a reading of the following detailed description in conjunction with the drawings wherein there is shown and described illustrative embodiments of the invention.

BRIEF DESCRIPTION OF DRAWINGS

This invention is described by appended claims in relation to description of a preferred embodiment with reference to the following drawings which are described briefly as follows:

FIG. 3 is a partially cutaway side elevation view of an air-circulator room deodorizer hanging from a room air circulator that is a horizontally oriented room fan;

FIG. 4 is a partially cutaway side elevation view of an air-circulator room deodorizer hanging from a room air circulator that is a wall air-conditioner vent;

FIG. 5 is a partially cutaway side elevation view of an air-circulator room deodorizer that is an ornament such as a Christmas tree hanging from a light chain of a ceiling fan;

FIG. 6 is a partially cutaway side elevation view of an air-circulator room deodorizer that has a flat intake-air surface;

FIG. 7 is a partially cutaway cross-sectional view taken through section line 7 from a top of the FIG. 6 illustration to show variable inlet for adjusting rate of airflow of room-circulation air;

DESCRIPTION OF PREFERRED EMBODIMENT

Figure 1:
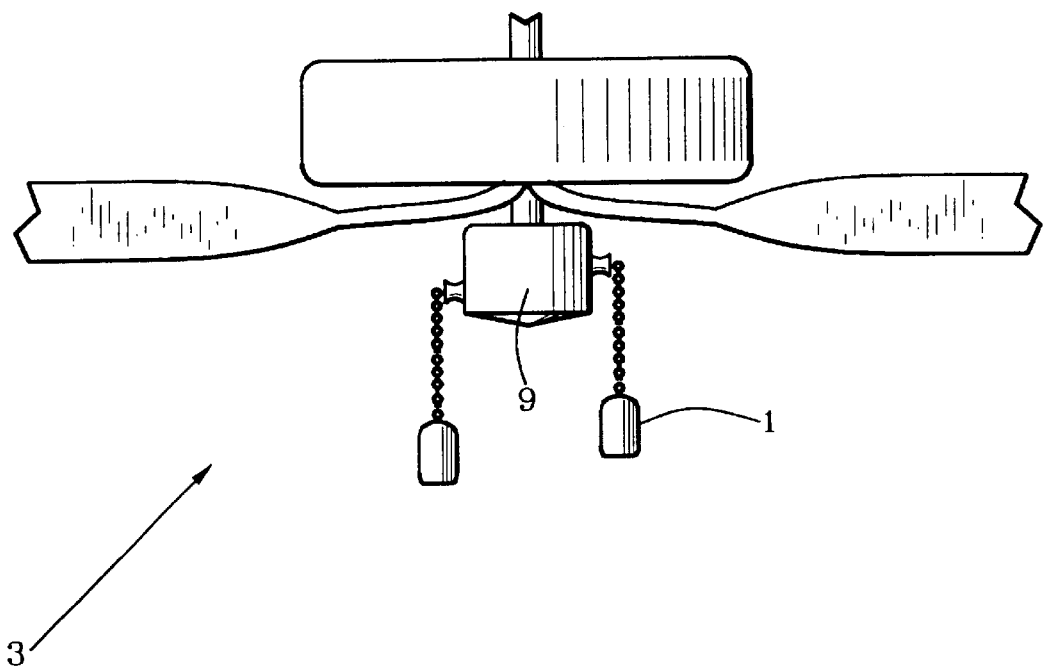
FIG. 1 is a partially cutaway side elevation view of an air-circulator room deodorizer hanging from a room air circulator that is a ceiling fan.

Listed numerically below with reference to the drawings are terms used to describe features of this invention. These terms and list numbers assigned to them designate the same features throughout this description.

1. Permeable container
2. Air-permeable surface
3. Ceiling fan
4. Celing vent
5. Horizontally oriented fan
6. Wall vent
7. Light chain
8. Ball-chain fastener
9. Fan control structure
10. Ceiling-vent fastener
11. Ceiling-vent member
12. Fan-shield fastener
13. Fan shield
14. Wall-vent fastener
15. Wall-vent member
16. Top
17. Sides
18. Deoderant pack
19. Sponge-like substance
20. Cupped base
21. Open area
22. Structural surface
23. Control blades
24. Control stators
25. Pack retainer
26. OD machine threading
27. ID machine threading
28. Knurled knob
29. Retainer latch
30. Latch boss
31. Retainer-latch passageway
32. Push-pull-turn knob Reference is made first to FIGS. 1–5. An air-circulator room deodorizer with a permeable container 1 having an air-permeable surface 2 is sized and shaped to be positioned in airflow from a room air circulator such as a ceiling fan 3 as depicted in FIG. 1, a ceiling vent 4 as depicted in FIG. 2, a horizontally oriented fan 5 as depicted in FIG. 3, or a wall vent 6 as depicted in FIG. 4.

Figure 2:
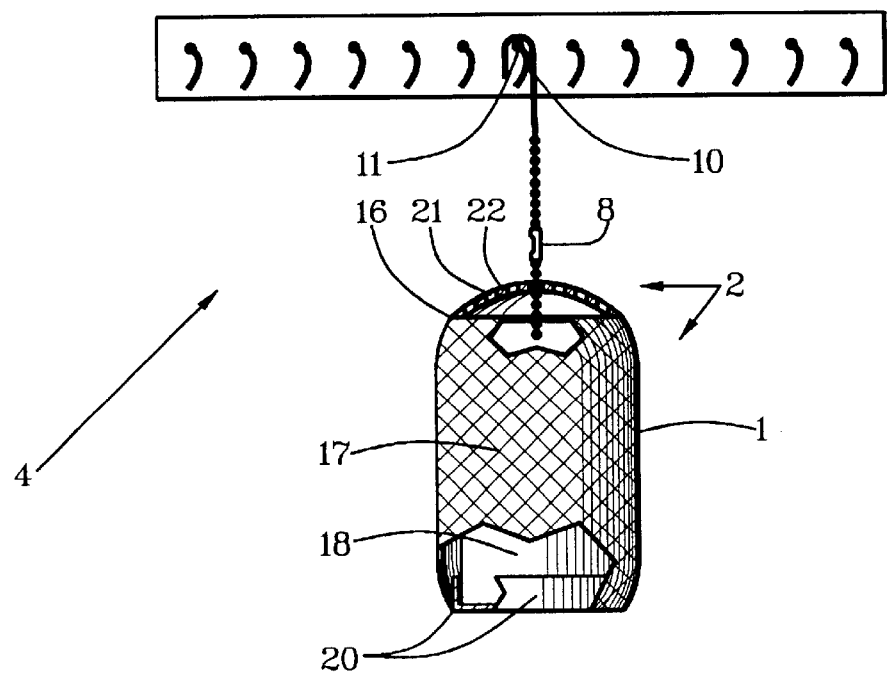
FIG. 2 is a partially cutaway side elevation view of an air-circulator room deodorizer hanging from a room air circulator that is a ceiling air-conditioner vent.

The permeable container 1 is attached detachably to the room air circulator with an air-circulator attachment such as a ball-chain fastener 8 attachable to the light chain 7 as shown in FIG. 5, the ball-chain fastener 8 attachable to a fan control structure 9 as shown in FIG. 1, a ceiling-vent fastener 10 for attachment to at least one appropriate ceiling-vent member 11 as shown in FIG. 2, a fan-shield fastener 12 for attachment to a fan-shield 13 as shown in FIG. 3, or a wall-vent fastener 14 for attachment to at least one appropriate wall-vent member 15 as shown in FIG. 4.

The air-permeable surface 2 can include a top 16 that is air pervious for inlet of vertical airflow and sides 17 that are air pervious for horizontal inlet of airflow. For dedication to horizontal-airflow use, the top 16 need not be air pervious. A lattice structure as depicted or other porous structure can be employed to allow air to flow into and out from the permeable container 1. The air-permeable surface 2 can be a surface of an ornament or icon such as represented by curvature, hemispherical and cylindrical structure in FIGS. 1–4, by conical structure in FIG. 5 and by flat structure in FIG. 6.

Figure 9:
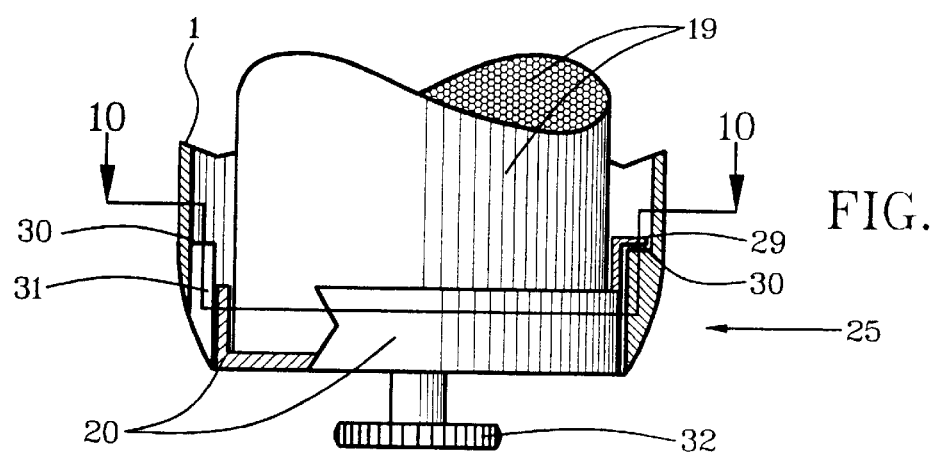
FIG. 9 is a partially cutaway side view of a bottom of an air-circulator room deodorizer having threaded connection of a pack retainer to a permeable container.
Figure 10:
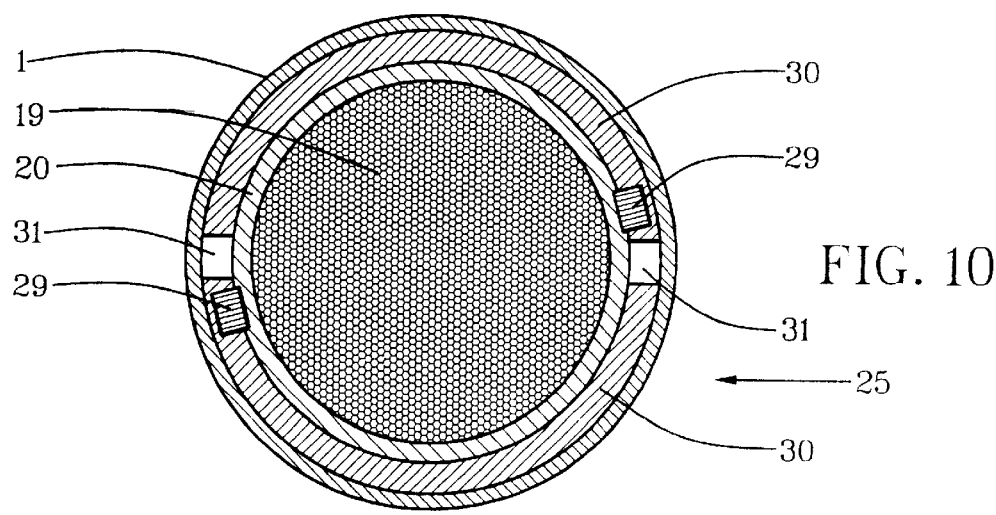
FIG. 10 is a cross-sectional view of FIG. 9 taken through section line 10.

A deodorant pack 18 having a desired fragrance in a desired host material fits inside of the permeable container 1. The host material can be a relatively rigid substance that gasifies to give off gaseous fragrance. Optionally as depicted in FIGS. 9–10, the host material can be a sponge-like substance 19 to absorb a liquid fragrance. The deodorant pack 18 can have a cupped base 20 for retaining liquid deodorant that might escape from overfilling of the sponge-like substance 19. The cupped base 20 also can provide structural support for a deodorant pack 18 which has a rigid host material. All deodorant packs 18 can have predetermined rates of evaporation of fragrance gasses for predetermined airflow through air-permeable surfaces 2 of the permeable container 1.

As depicted in FIG. 5, the conical structure of air-permeable surface 2 is depicted in a Christmas tree form with a deodorant pack 18 having a matching structure to demonstrate ornamental uses of this air-circulator room deodorizer.

This air-circulator room deodorizer is intended for variously colorful, festive and solemn decoration. It enhances impact of any occasion, of everyday living and of the workplace with fragrant room air circulation. Hence the representation of selection of shapes and positioning in airflow of room air circulation.

As shown in FIGS. 1–4, a combined open area 21 of permeability in the air-permeable surface 2 in proportion to structural surface 22 can be fixed or, as depicted in FIG. 7, it can be variable.

Referring to FIGS. 6–7 for variation of open area 21, control blades 23 are rotated selectively between open mode when rotated to positions under control stators 24 and closed mode when rotated from under the control stators 24 to positions that close the open areas 21. This is a deodorant-control structure for controlling release of deodorant by controlling action of airflow on the deodorant pack 18. It is a controlled covering of the air-permeable surface 2 of a top 16 that is flat. Similarly variable covering structure can be provided for sides 17 of permeable containers 1.

Figure 8:
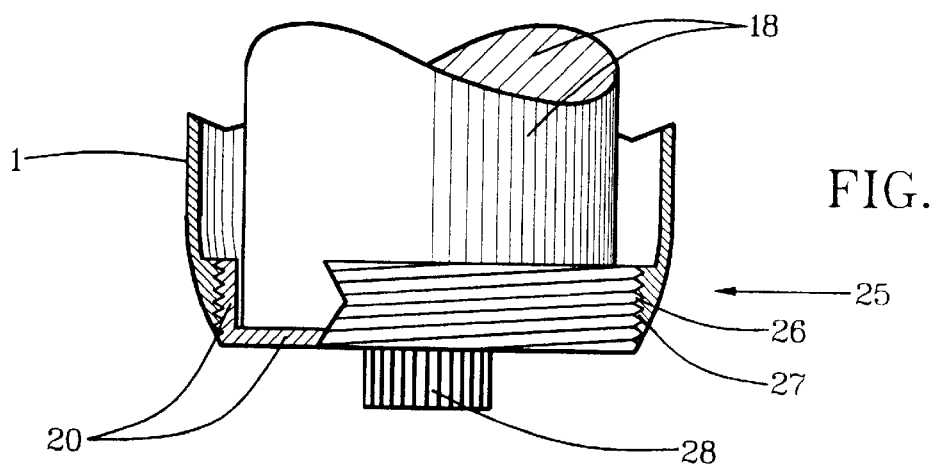
FIG. 8 is a partially cutaway side view of a bottom of an air-circulator room deodorizer having threaded connection of a pack retainer to a permeable container.

Referring to FIG. 8 in relation to retaining the cupped base 20 in the permeable container 1, a pack retainer 25 has a circumferential base with at least partial-rotation outside-diameter (OD) machine threading 26 on an outside periphery of a circumferential base, such as on walls of the cupped base 20. Correspondingly, a bottom portion of the permeable container 1 can have inside-diameter (ID) machine threading 27 that matches the OD machine threading 26 for a full-threading or a part-circle threading to hold the cupped base 20 in the permeable container 1. A knurled knob 28 can be positioned on a bottom of the cupped base 20 for thread-rotational positioning of the cupped base 20 in the permeable container 1.

Referring to FIGS. 9–10 in relation to quick-disconnect attachment of the cupped base 20 to the permeable container 1, the pack retainer 25 can have at least one retainer latch 29 with a horizontal projection on an outside periphery of the circumferential base. An inside circumferential periphery of a bottom portion of the permeable container 1 has a latch boss 30 with a horizontal surface that is sized and shaped to support the retainer latch 29. The latch boss 30 is preferably a horizontal platform that is preferably arcuate or circumferential on at least one side of a retainer-latch passageway 31 that is oriented linearly to an axis of the permeable container 1. A push-pull-turn knob 32 can be provided on the bottom of the cupped base 20 for inserting the cupped base 20 into the bottom of the permeable container 1 with the retainer latch 29 in the retainer-latch passage 31 and then rotating it slightly to position the retainer latch 29 on the latch boss 30. Quick-disconnect removal of the cupped base 20 is accomplished by slight rotation to reposition the retainer latch 29 in the retainer-latch passageway 31 and then pulling it out.

A new and useful air-circulator room deodorizer having been described, all such foreseeable modifications, adaptations, substitutions of equivalents, mathematical possibilities of combinations of parts, pluralities of parts, applications and forms thereof as described by the following claims and not precluded by prior art are included in this invention.

What is claimed is:

1. An air-circulator room deodorizer comprising:

a permeable container having an air-permeable surface;

the permeable container being sized and shaped to be positioned in airflow from a room air circulator;

an air-circulator attachment with which the permeable container is attached detachably to the room air circulator;

the air-permeable surface facing into the airflow;

a deodorant pack that fits inside of the permeable container; and a pack retainer intermediate the permeable container and the deodorant pack to retain the deodorant pack at a predetermined position in the permeable container, wherein the room air circulator is a ceiling fan and the air-circulator attachment is a ball-chain fastener attachable intermediate the permeable container and a light chain extended from the ceiling fan.

2. An air-circulator room deodorizer as described in claim 1 wherein:

at least the air-permeable surface of the permeable container is a latticed structure.

3. An air-circulator room deodorizer as described in claim 1 wherein:

the air-permeable surface is a surface of a decorative item having a predetermined area of structural material in proportion to a combined open area of permeability in the air-permeable surface.

4. An air-circulator room deodorizer as described in claim 3 wherein:

the combined open area of the permeability in the air-permeable surface is fixed in proportion to the predetermined area of the structural material of the air-permeable surface.

5. An air-circulator room deodorizer as described in claim 1 wherein:

the combined open area for the permeability in the air-permeable surface is variable in proportion to the predetermined area of the structural material of the air-permeable surface.

6. An air-circulator room deodorizer as described in claim 5 wherein:

the combined open area for the permeability in the air-permeable surface is variable manually in proportion to the predetermined area of the structural material of the air-permeable surface.

7. An air-circulator room deodorizer as described in claim 6 wherein:

a control cover having at least one cover perforation is manipulated by manual orientation of the control cover to position the cover perforation in line with at least one container perforation in the air-permeable surface selectively for manual variation of the combined open area for the permeability in the air-permeable surface in proportion to the predetermined area of the structural material of the air-permeable surface.

8. An air-circulator room deodorizer as described in claim 7 wherein:

the control cover is positioned pivotally on the permeable container.

9. An air-circulator room deodorizer as described in claim 1 wherein:

the air-permeable surface is hemispherical with an apex facing the airflow.

10. An air-circulator room deodorizer as described in claim 1 wherein:

the air-permeable surface is conical with an apex facing the airflow.

11. An air-circulator room deodorizer as described in claim 1 wherein:

the air-permeable surface is flat.

12. An air-circulator room deodorizer as described in claim 1 wherein:

the deodorant pack includes a sponge-like material with predetermined absorption and release of deodorant having predetermined liquidity and evaporative rate.

13. An air-circulator room deodorizer as described in claim 12, wherein:

the pack retainer has a cupped base for retaining liquid deodorant escaping from the sponge-like material when overfilled with the liquid deodorant.

14. An air-circulator room deodorizer as described in claim 1 wherein:

the deodorant pack includes a rigid deodorant material having predetermined evaporative rate.

15. An air-circulator room deodorizer as described in claim 1 and further comprising:

deodorant-control structure for controlling release of deodorant by action of the airflow on the deodorant pack.

16. An air-circulator room deodorizer as described in claim 15 wherein:

the deodorant-control structure is controlled covering of predetermined air-permeable surface of the permeable container.

17. An air-circulator room deodorizer comprising:

a permeable container having an air-permeable surface;

the permeable container being sized and shaped to be positioned in airflow from a room air circulator;

an air-circulator attachment with which the permeable container is attached detachably to the room air circulator;

the air-permeable surface facing into the airflow;

a deodorant pack that fits inside of the permeable container; and a pack retainer intermediate the permeable container and the deodorant pack to retain the deodorant pack at a predetermined position in the permeable container, wherein the pack retainer has a circumferential base with at least partial-rotation outside-diameter machine threading on an outside periphery of the circumferential base; and the permeable container has a bottom portion with an inside circumferential periphery having at least partial-rotation inside-diameter machine threading that is sized and shaped to receive the outside-diameter machine threading on the circumferential base of the pack retainer.

18. An air-circulator room deodorizer comprising:

a permeable container having an air-permeable surface;

the permeable container being sized and shaped to be positioned in airflow from a room air circulator;

an air-circulator attachment with which the permeable container is attached detachably to the room air circulator;

the air-permeable surface facing into the airflow;

a deodorant pack that fits inside of the permeable container; and a pack retainer intermediate the permeable container and the deodorant pack to retain the deodorant pack at a predetermined position in the permeable container wherein the pack retainer has a circumferential base with at least one retainer latch on an outside periphery of the circumferential base;

the permeable container has a bottom portion with an inside circumferential periphery having at least one latch boss that is sized and shaped to contain the retainer latch; and the latch boss has a horizontal platform on at least one side of a retainer-latch passageway that is oriented linearly to an axis of the permeable container, such that the circumferential base of the pack retainer can be inserted into the inside circumferential periphery of the bottom of the permeable retainer with the retainer latch passing through the retainer-latch passageway and then being rotated to a position on the latch boss.

19. An air-circulator room deodorizer comprising:

a permeable container having an air-permeable surface;

the permeable container being sized and shaped to be positioned in airflow from a room air circulator;

an air-circulator attachment with which the permeable container is attached detachably to the room air circulator;

the air-permeable surface facing into the airflow;

a deodorant pack that fits inside of the permeable container; and a pack retainer intermediate the permeable container and the deodorant pack to retain the deodorant pack at a predetermined position in the permeable container;

the room air circulator is a ceiling fan; and the air-circulator attachment is a fan-housing fastener attachable intermediate the permeable container and a fan housing vertically beneath the ceiling fan.

20. An air-circulator room deodorizer as described in claim 19, wherein:

at least the air-permeable surface of the permeable container is a latticed structure.

21. An air-circulator room deodorizer as described in claim 19 wherein:

the air-permeable surface is a surface of a decorative item having a predetermined area of structural material in proportion to a combined open area of permeability in the air-permeable surface.

22. An air-circulator room deodorizer as described in claim 21 wherein:

the combined open area of the permeability in the air-permeable surface is fixed in proportion to the predetermined area of the structural material of the air-permeable surface.

23. An air-circulator room deodorizer as described in claim 19 wherein:

the combined open area for the permeability in the air-permeable surface is variable in proportion to the predetermined area of the structural material of the air-permeable surface.

24. An air-circulator room deodorizer as described in claim 23 wherein:

the combined open area for the permeability in the air-permeable surface is variable manually in proportion to the predetermined area of the structural material of the air-permeable surface.

25. An air-circulator room deodorizer as described in claim 24 wherein:

a control cover having at least one cover perforation is manipulated by manual orientation of the control cover to position the cover perforation in line with at least one container perforation in the air-permeable surface selectively for manual variation of the combined open area for the permeability in the air-permeable surface in proportion to the predetermined area of the structural material of the air-permeable surface.

26. An air-circulator room deodorizer as described in claim 25 wherein:

the control cover is positioned pivotally on the permeable container.

27. An air-circulator room deodorizer as described in claim 19 wherein:

the air-permeable surface is hemispherical with an apex facing the airflow.

28. An air-circulator room deodorizer as described in claim 19 wherein:

the air-permeable surface is conical with an apex facing the airflow.

29. An air-circulator room deodorizer as described in claim 19 wherein:

the air-permeable surface is flat.

30. An air-circulator room deodorizer as described in claim 19 wherein:

the deodorant pack includes a sponge-like material with predetermined absorption and release of deodorant having predetermined liquidity and evaporative rate.

31. An air-circulator room deodorizer as described in claim 30 wherein:

the pack retainer has a cupped base for retaining liquid deodorant escaping from the sponge-like material when overfilled with the liquid deodorant.

32. An air-circulator room deodorizer as described in claim 19 wherein:

the deodorant pack includes a rigid deodorant material having predetermined evaporative rate.

33. An air-circulator room deodorizer as described in claim 19 and further comprising:

deodorant-control structure for controlling release of deodorant by action of the airflow on the deodorant pack.

34. An air-circulator room deodorizer as described in 33 wherein:

the deodorant-control structure is controlled covering of predetermined air-permeable surface of the permeable container.

35. An air-circulator room deodorizer as described in claim 19 wherein:

the pack retainer has a circumferential base with at least partial-rotation outside-diameter machine threading on an outside periphery of the circumferential base; and the permeable container has a bottom portion with an inside circumferential periphery having at least partial-rotation inside-diameter machine threading that is sized and shaped to receive the outside-diameter machine threading on the circumferential base of the pack retainer.

36. An air-circulator room deodorizer as described in claim 19 wherein:

the pack retainer has a circumferential base with at least one retainer latch on an outside periphery of the circumferential base;

the permeable container has a bottom portion with an inside circumferential periphery having at least one latch boss that is sized and shaped to contain the retainer latch; and the latch boss has a horizontal platform on at least one side of a retainer-latch passageway that is oriented linearly to an axis of the permeable container, such that the circumferential base of the pack retainer can be inserted into the inside circumferential periphery of the bottom of the permeable retainer with the retainer latch passing through the retainer-latch passageway and then being rotated to a position on the latch boss.

* * * * *